US012064086B1

United States Patent
Gist

(10) Patent No.: US 12,064,086 B1
(45) Date of Patent: Aug. 20, 2024

(54) ENDOSCOPY DEVICE HAVING FLUID CONTROL MECHANISMS

(71) Applicant: EvoEndo, Inc., Centennial, CO (US)

(72) Inventor: Jahi Carlos Gist, Barrington, IL (US)

(73) Assignee: EVOENDO, INC.

( * ) Notice: Subject to any disclaimer, the term of this patent is extended or adjusted under 35 U.S.C. 154(b) by 4 days.

(21) Appl. No.: 18/108,558

(22) Filed: Feb. 10, 2023

(51) Int. Cl.
| | | |
|---|---|---|
| *A61B 1/015* | (2006.01) | |
| *A61B 1/00* | (2006.01) | |
| *A61B 1/018* | (2006.01) | |
| *A61B 1/05* | (2006.01) | |
| *A61B 1/06* | (2006.01) | |
| *A61B 1/233* | (2006.01) | |

(52) U.S. Cl.
CPC .......... *A61B 1/015* (2013.01); *A61B 1/00018* (2013.01); *A61B 1/00042* (2022.02); *A61B 1/00045* (2013.01); *A61B 1/018* (2013.01); *A61B 1/05* (2013.01); *A61B 1/0676* (2013.01); *A61B 1/233* (2013.01)

(58) Field of Classification Search
CPC ......... A61B 1/015; A61B 1/018; A61B 1/012; A61B 1/12; A61B 1/126–128; A61B 1/233; A61B 1/00112; A61B 1/00119; A61B 1/00121; A61B 1/00087; A61B 1/0008; A61B 1/00071; A61B 1/00128; A61B 1/00068; A61B 1/00091; A61B 1/125; A61B 1/00094; A61B 1/00064; A61B 1/00066
USPC .......................... 600/104, 153–155, 158–159
See application file for complete search history.

(56) References Cited

U.S. PATENT DOCUMENTS

| | | | | |
|---|---|---|---|---|
| 4,800,869 A | * | 1/1989 | Nakajima .......... | A61B 1/00068 600/158 |
| 6,309,347 B1 | * | 10/2001 | Takahashi .............. | A61B 1/015 600/159 |
| 8,915,842 B2 | * | 12/2014 | Weisenburgh, II .. | A61B 1/3132 600/156 |
| 2012/0130174 A1 | * | 5/2012 | Simmons .............. | A61M 1/774 600/159 |
| 2013/0274550 A1 | * | 10/2013 | Takeuchi ............... | A61B 1/015 600/104 |

(Continued)

Primary Examiner — Ryan N Henderson
Assistant Examiner — Pamela F Wu
(74) Attorney, Agent, or Firm — Farber LLC

(57) ABSTRACT

Systems and methods are disclosed for an endoscope for use in a surgical procedure, e.g., a pediatric trans-nasal endoscopy procedure. The endoscope may include a handle for gripping by a user, and a shaft extending from the handle. The shaft may have a working channel extending longitudinally therethrough and a distal region configured to be inserted into a patient. A fluid control mechanism on the handle may be actuatable by a user to selectively control the flow of at least one of air, suction or water through the working channel. The working channel may include a bifurcation region that splits the working channel into a first channel through which a surgical instrument can be introduced into the working channel, and a second channel configured to selectively convey at least one of air, suction or water into the working channel. A tubing set may be connected to the handle, the tubing set including a second air tube that may be configured to convey air from an air source to a water source so as to pressurize the water source and thereby push water from the water source towards the working channel.

17 Claims, 7 Drawing Sheets

(56) References Cited

U.S. PATENT DOCUMENTS

| | | | |
|---|---|---|---|
| 2015/0216393 A1* | 8/2015 | Toyoda | A61B 1/00068 |
| | | | 600/159 |
| 2020/0154981 A1* | 5/2020 | Mankowski | A61B 1/00101 |
| 2021/0076914 A1* | 3/2021 | Arai | A61B 1/00119 |
| 2022/0125283 A1* | 4/2022 | Kress | A61B 1/00105 |

* cited by examiner

US 12,064,086 B1

ENDOSCOPY DEVICE HAVING FLUID CONTROL MECHANISMS

BACKGROUND

Eosinophilic esophagitis (EoE) is an increasingly common chronic inflammatory disease that affects children and adults. Because of its potential to progress to esophageal stricture and the fact that symptoms do not always correlate with degree of eosinophilia, much attention has been paid to repeated assessment of the esophageal mucosa to ensure mucosal healing following treatment. In contrast, the risks, cost and time commitment associated with traditional sedated esophagogastroduodenoscopy (EGD) can be significant and have raised concerns for providers and patients alike. To address these questions, alternative methods are needed to measure esophageal inflammation. In addition to esophagoscopy with biopsies, other technologies such as the Cytosponge, esophageal string test and confocal tethered endomicroscopy have emerged as potential alternatives for assessing mucosal inflammation.

Recent work has led to the development of trans-nasal endoscopy/esophagoscopy (TNE) to assess the esophageal mucosa in adults. In contrast to traditional EGDs, TNE offers advantages, including that it can be performed in an outpatient clinic room, requires no anesthesia or sedation, uses an adult trans-nasal gastroscope that is tolerated by adults and procures samples adequate for assessment of Barrett's Esophagus. However, the endoscopes used in the adult procedures are not appropriate for use in pediatric setting and, in fact, may be too large for many adults.

During a trans-nasal endoscopic procedure, patients may experience physical discomfort due to the endoscope being inserted into the nose, through the sinus cavities and down into the esophagus. This physical discomfort, or even the fear of being uncomfortable, can make trans-nasal endoscopy procedures mentally and emotionally distressing for a patient, too. Because it is desirable to make the procedure mentally and physically easier on the patient, it would be advantageous to optimize the endoscope being used for the procedure.

SUMMARY

The following presents a simplified summary of the claimed subject matter in order to provide a basic understanding of some aspects of the claimed subject matter. This summary is not an extensive overview of the claimed subject matter. It is intended to neither identify key or critical elements of the claimed subject matter nor delineate the scope of the claimed subject matter. Its sole purpose is to present some concepts of the claimed subject matter in a simplified form as a prelude to the more detailed description that is presented later.

The trans-nasal endoscope described hereinbelow, according to various embodiments, addresses various challenges. For example, the trans-nasal endoscope described hereinbelow, according to various embodiments, provides a device and associated methodology that can be used to adapt TNE to assess the esophageal mucosa, gastric, and duodenal, tracheal, and bronchial mucosa in children and small adults in both a sedated and unsedated manner with a full array of steering and visualization capabilities. The trans-nasal endoscope described hereinbelow, according to various embodiments, provides a scope that minimizes the outer diameter thereof, e.g., to reduce the discomfort to patients, while maximizing the diameter of the working channel, e.g., to provide the largest possible channel through which tools may be introduced, while simultaneously providing enhanced, e.g., four-way, steering capabilities as well as visualization functionality, as will be described more fully below. In various embodiments, the outer diameter of the endoscope shaft may be less than about 4.5 mm, and preferably is about 3.5 mm. In addition, in various embodiments, the diameter of the working channel may have a range of about 1.5 mm to 2.5 mm, and preferably is about 2.0 mm.

It is noted that, according to various embodiments, the endoscope described herein may be particularly well-suited for unsedated surgical procedures. Sedation is well-known, in certain circumstances, to present various risks to patients, but is often employed during surgical procedures to prevent a patient from experiencing discomfort or anxiety. By providing an endoscope having, e.g., a minimized outer diameter, a more flexible and more steerable distal regions (as will be explained in further detail below) among other advantages described below, patient discomfort and anxiety may be reduced, thereby enabling surgical procedures to be performed in an unsedated, and thus more safe, manner.

It should be recognized that, while the scope set forth herein is described hereinbelow for use in a trans-nasal endoscopy procedure, it may also be employed in a variety of other medical or surgical applications. For example, the scope set forth herein may be employed for use as a nasal endoscope, a trans-nasal esophagoscope, a trans-nasal gastroscope, a trans-nasal duodenoscope, a trans-nasal enteroscope, a triple endoscope, a bronchoscope, a laryngoscope, a trans-nasal gastroscope, an aerodigestive scope, and/or an endoscopic device used to visualize any body cavity into which it would fit, e.g., for examination of a stricture or the like. It should also be recognized that the endoscope described herein may be employed in fetal surgical procedures, and/or in surgical procedures that employ natural orifices, e.g., NOTES or natural orifice transluminal endoscopic procedures, such as trans-orally, trans-anally, trans-vaginally or any other natural orifice. The discussion herein of a pediatric trans-nasal endoscopy procedure is merely exemplary.

In accordance with various embodiments thereof, systems and methods are provided for use in a surgical procedure. In an embodiment, there is provided an endoscope for use in a surgical procedure, e.g., a pediatric trans-nasal endoscopy procedure, that includes a handle for gripping by a user, and a shaft extending from the handle. The shaft may have a working channel extending longitudinally therethrough. The shaft may also have a proximal region at or adjacent to the handle and a distal region configured to be inserted into a patient. In an embodiment, the endoscope may also include a fluid control mechanism on the handle actuatable by a user to selectively control the flow of at least one of air, suction or water through the working channel. Advantageously, the fluid control mechanism is actuatable by a user to selectively control the flow of all three of air, suction and water through the working channel.

In embodiments, the fluid control mechanism may include three valves. A first valve may be actuatable by a user to selectively control the flow of air through the working channel. A second valve may be actuatable by a user to selectively control the flow of suction through the working channel. A third valve may be actuatable by a user to selectively control the flow of water through the working channel. Each of the first, second and third valves may include an inlet connected to a respective source of air, suction and water, and an outlet connected to the working channel.

Each of the first, second and third valves may also include a sealing element that, when the valve is in a rest position, is in a closed position at which the inlet opening is not connected to the outlet opening. Each of the first, second and third valves may also include a spring that biases the valves toward their respective resting positions. Each such spring may have a button mounted thereto that, upon being pressed by a user, overcomes the bias of the spring to move the sealing element from the closed position to an open position at which the inlet opening is connected to the outlet opening to thereby permit flow from the respective source of air, suction or water into and through the working channel.

In addition, the working channel may include an instrument port through which a surgical instrument can be introduced into and through the working channel. In various embodiments, the working channel may include a bifurcation region that splits the working channel into a first channel and a second channel. The first channel may have an instrument port through which a surgical instrument can be introduced into the working channel. The second channel may be connected to the control mechanism on the handle for selectively conveying the at least one of air, suction or water into the working channel.

The endoscope may also include an illumination source and an imaging device located at the distal end of the shaft. Functions of the illumination source and the imaging device may be controlled by an electronic control module that is adjacent to the fluid control mechanism on the handle.

In still other embodiments, there is provided an endoscope for use in a surgical procedure, e.g., a pediatric trans-nasal endoscopy procedure. The endoscope may include a handle for gripping by a user, and a shaft extending from the handle. The shaft may have a working channel extending longitudinally therethrough, and a distal region configured to be inserted into a patient. The working channel may include a bifurcation region that splits the working channel into a first channel and a second channel. The first channel may have an instrument port through which a surgical instrument can be introduced into the working channel. The second channel may be configured to selectively convey at least one of air, suction or water into the working channel.

In embodiments, the instrument port may include a valve through which the surgical instrument can be introduced. The instrument port valve may be configured to prevent flow of air, water or suction through the first channel when a surgical instrument is present within the first channel and when an instrument is not present in the first channel. The instrument port may be configured to receive, e.g., a biopsy forceps instrument therethrough and into the working channel.

Still further, the endoscope may also include a fluid control mechanism on the handle. The fluid control mechanism may be actuatable by a user to selectively control the flow of the at least one of air, suction or water, and advantageously all three, into the second channel and the working channel. The fluid control mechanism may include a first valve actuatable by a user to selectively control the flow of air through the working channel, a second valve actuatable by a user to selectively control the flow of suction through the working channel, and a third valve actuatable by a user to selectively control the flow of water through the working channel.

In embodiments, each of the first, second and third valves may include an inlet connected to a respective source of air, suction and water, and an outlet connected to the second channel. Still further, each of the first, second and third valves may include a spring-biased sealing element that is in a closed position preventing flow from the inlet to the outlet until a user presses a button to overcome the spring and move the sealing element to an open position allowing flow from the inlet to the outlet.

The endoscope may also include an illumination source and an imaging device located at the distal end of the shaft. The illumination source and the imaging device may be controlled by an electronic control module that is adjacent to the fluid control mechanism on the handle.

In still further embodiments, there is provided an endoscope for use in a surgical procedure, e.g., a pediatric trans-nasal endoscopy procedure, that includes a handle for gripping by a user, and a shaft extending from the handle. The shaft may have a working channel extending longitudinally therethrough, and a distal region configured to be inserted into a patient. In embodiments, the endoscope may also include a tubing set connected to the handle. The tubing set may include a suction tube configured to generate suction in the working channel. The tubing set may also include a water tube configured to convey water from a water source towards the working channel. The tubing set may also include a first air tube configured to convey air from an air source to the working channel. Still further, the tubing may include a second air tube that is configured to convey air from the air source to the water source so as to pressurize the water source and thereby push water from the water source towards the working channel. In embodiments, the water source is a water bottle. The water bottle may have a cap that defines a first connection to the water tube and a second connection to the second air tube.

In embodiments, the endoscope may also include a fluid control mechanism on the handle. The fluid control mechanism may be actuatable by a user to selectively control the flow of the air from the air source to the working channel, the flow of suction from the working channel to a suction source, and the flow of water from the water source to the working channel. The fluid control mechanism may include a first valve actuatable by a user to selectively control the flow of air through the working channel, a second valve actuatable by a user to selectively control the flow of suction through the working channel, and a third valve actuatable by a user to selectively control the flow of water through the working channel. In addition, in embodiments, each of the first, second and third valves may include an inlet connected to a respective source of air, suction and water, and an outlet connected to the second channel. Still further, each of the first, second and third valves may include a spring-biased sealing element that is in a closed position preventing flow from the inlet to the outlet until a user presses a button to overcome the spring and move the sealing element to an open position allowing flow from the inlet to the outlet.

Still further, the tubing set may also include a video connector cable. The endoscope may include an illumination source and an imaging device located at the distal end of the shaft. The illumination source and the imaging device may be connected to, and controlled by an electronic control module on the handle. The video connector cable may be configured to convey signals from the electronic control module on the handle to an external video display device.

It should be noted, of course, that to the extent that images, e.g., image signals, image data, etc., are described herein, it will be understood that such also refers to video, e.g., video signals, video data, etc., and that the description of the image signals is intended to include single images, still images, video images, etc. without limitation.

DRAWINGS

DETAILED DESCRIPTION

Reference will now be made in detail to specific embodiments illustrated in the accompanying drawings. In the following detailed description, numerous specific details are set forth to provide a thorough understanding. However, it will be apparent to one of ordinary skill in the art that embodiments may be practiced without these specific details. In other instances, known methods, procedures, components, circuits, and networks have not been described in detail so as not to unnecessarily obscure aspects of the embodiments.

Figure 1:
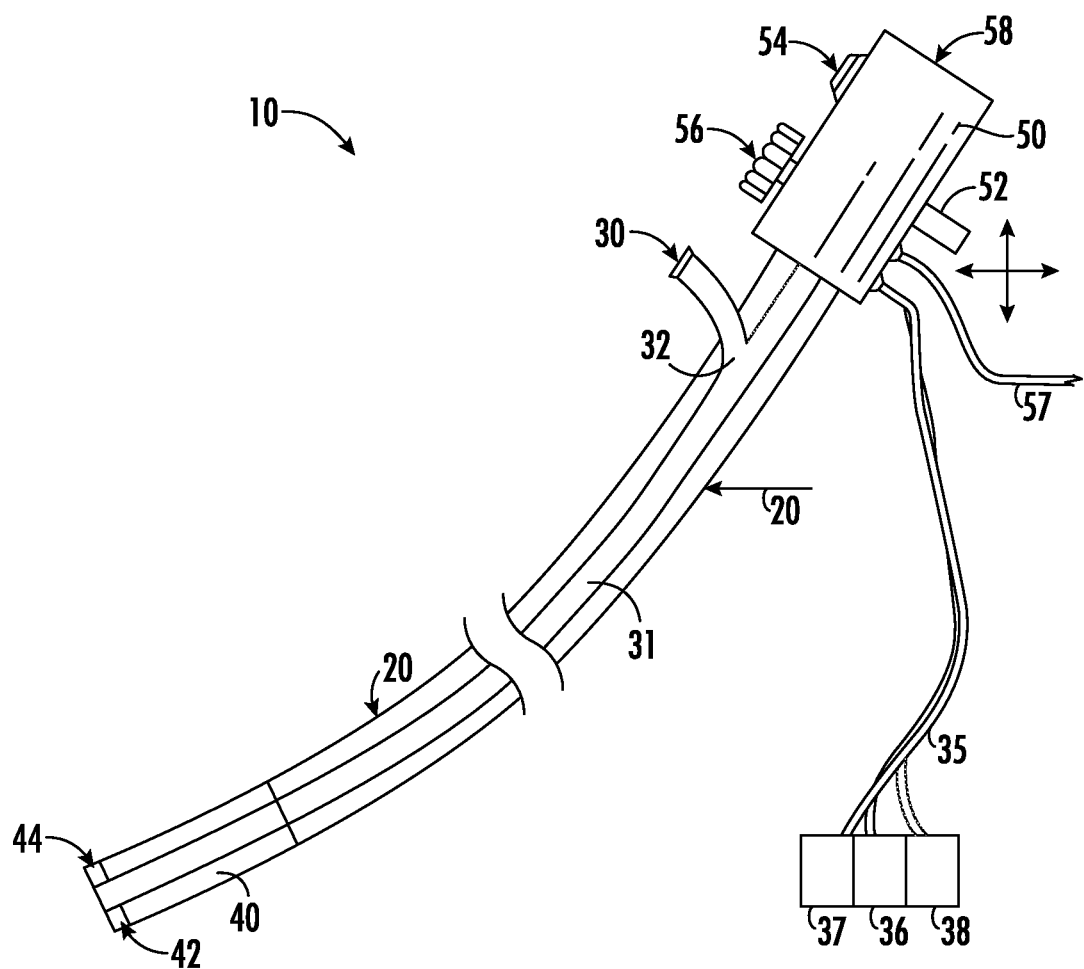
FIG. 1 shows a schematic representation of a trans-nasal endoscope that includes a flexible endoscope shaft, in accordance with various embodiments.

FIG. 1 is a schematic diagram of a trans-nasal endoscope 10, according to one example embodiment, illustrating some of the various features thereof. As mentioned previously, while the example embodiments set forth hereinbelow are described as an endoscope that is suitable for trans-nasal insertion into a patient, and is particularly well-suited for trans-nasal insertion into a child or small adult, it is understood that this is merely one example embodiment, and that the description hereinbelow of a trans-nasal endoscope does not preclude the use of the device in other types of procedures and for other types of patients. It should be noted that FIG. 1 is merely schematic, and thus the shape and position of the various features illustrated therein are merely exemplary. Additional figures, illustrating specific embodiments of the various features and functionality, will be provided in further detail below.

In the embodiment shown schematically in FIG. 1, the trans-nasal endoscope 10 includes a flexible endoscope shaft 20. The flexible endoscope shaft 20 has a working channel 31. The working channel 31 extends longitudinally from a distal end 40 of the endoscope shaft 20 proximally towards a handle 50 located at or near the proximal end of the trans-nasal endoscope 10. At, within or near the handle 50, the working channel 31 has a bifurcation region 32. Proximal to the bifurcation region 32, the working channel 31 splits into two channels. A first portion of the working channel 31 proximal to the bifurcation regions 32 extends towards an instrument insertion port 30 suitable for, e.g., conducting a biopsy therethrough. The instrument insertion port 30 allows an instrument, e.g., a pediatric nasal endoscope biopsy forceps or other medical device, to be inserted through the bifurcation region 32 and to, and past, the distal end 40 of the endoscope shaft 20 so as to perform a procedure, e.g., a biopsy procedure, on tissue located at or near to the distal end 40 of the endoscope shaft 20.

A second portion of the working channel 31 proximal to the bifurcation regions 32 extends towards an air, water and suction (AWS) control mechanism 52. The AWS control mechanism 52 includes various valves (not shown in this view, but shown and described in connection with FIGS. 5 and 6) that allow selective connection of the working channel 31 to the AWS tubing set 35. The AWS tubing set 35 may include one or more flexible tubes (shown and described separately and in greater detail below in connection with FIG. 7. The AWS tubing set 35 may be connected to a water source 37 for supplying water through the working channel 31, to a suction source 36 for supplying suction through the working channel 31, and/or to an air source 38 for supplying air through the working channel 31, depending upon a user's selection via the AWS control mechanism 52. More specifically, the AWS control mechanism allows a user to direct one or more of air, suction or water through, e.g., the bifurcation region 32 and to, and past, the distal end 40 of the endoscope shaft 20 so as to enable their use during the performance of a procedure on tissue located at or near to the distal end 40 of the endoscope shaft 20.

The distal end 40 of the endoscope shaft 20 also includes an illumination source 42 to provide light at the distal tip 40. In embodiments, the illumination source 42 may be connected to and at least partially controllable by an electronics control module 54 located in the handle 50. The distal end 40 of the endoscope shaft 20 also includes an image capture device 44 to convey image or video signals related to the region of the distal end 40 of the endoscope shaft 20. In embodiments, the image capture device 44 may also be connected to and at least partially controllable by the electronics control module 54 located in the handle 50. The handle 50 may also include a shaft steering mechanism 56 to control or steer the lateral displacement at the distal end 40 of the endoscope shaft 20. In addition, the handle 50 may include a video display output 57, which may be connected to and output image data to a separate image or video display or control unit (not shown in this view).

Figure 2:
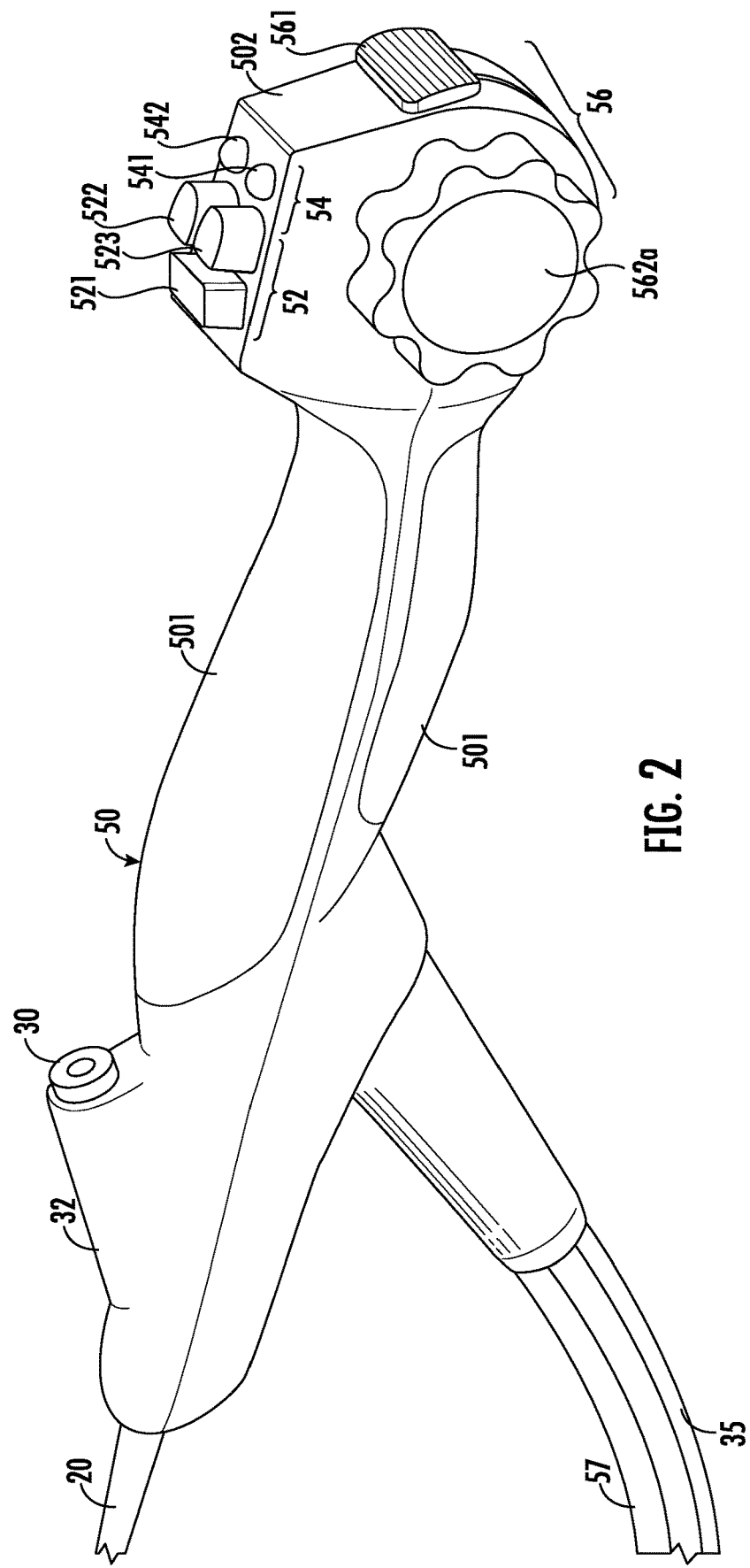
FIG. 2 is a perspective view of the handle of the trans-nasal endoscope, in accordance with various embodiments.

FIG. 2 is a perspective view of an example embodiment of the handle 50 of the trans-nasal endoscope 10. In this embodiment, the features and functionality that were shown schematically in FIG. 1 are provided in more detail, showing additional advantages thereof. For example, in this embodiment, the handle 50 of the trans-nasal endoscope 10 includes a gripping region 501 sized and contoured to fit comfortably in a user's hand. Located distally relative to the gripping region 501 is the bifurcation region 32. From the distalmost end of the bifurcation region 32 extends the flexible endoscope shaft 20, having a portion of the working channel 31 extending therethrough. The working channel 31 extends from the distal end 40 of the endoscope shaft 20, and splits into two channels in the bifurcation region 32. A first portion of the working channel 31 extends towards the instrument insertion port 30, which is suitable for receiving an instrument, e.g., a pediatric nasal endoscope biopsy forceps or other medical device, therethrough. The second portion of the working channel 31 proximal to the bifurcation region 32 extends proximally through the interior of the gripping region 501.

Proximal to the gripping region 501 is a control region 502 sized and shaped to extend beyond the heel of the user's hand when the palm of the user's hand is gripping the gripping region 501, enabling the control features positioned on the control region 502 to be engaged by the user's second hand when the user's first hand is gripping the gripping region 501.

In the embodiment shown in FIG. 2, the control region 502 has various control features positioned thereon. For example, the control region 502 has the AWS control mechanism 52. As set forth above, the AWS control mechanism 52 includes various features, e.g., buttons, valves, etc., that allow selective connection of the air, water and suction supply sources 36, 37, 38 to the working channel 31 via respective flexible tubes of the AWS tubing set 35. In the embodiment shown in FIG. 2, the AWS control mechanism 52 includes an air supply control button 521. The air supply control button 521 functions to selectively connect the air source 38 to the working channel 31, as will be described in greater detail below in connection with FIGS. 5 and 6.

In the embodiment shown in FIG. 2, the AWS control mechanism 52 also includes a water supply control button 522. The water supply control button 522 functions to selectively connect the water source 37 to the working channel 31, as will be described in greater detail below in connection with FIGS. 5 and 6.

Still further, in the embodiment shown in FIG. 2, the AWS control mechanism 52 includes a suction supply control button 523. The suction supply control button 523 functions to selectively connect the suction source 36 to the working channel 31, as will be described in greater detail below in connection with FIGS. 5 and 6.

In the embodiment shown in FIG. 2, the control region 502 also has the electronics control mechanism 54. As set forth above, the electronics control mechanism 54 includes various features, e.g., buttons, electrical connections, etc., that allow selective operation of, e.g, the image capture device 44 and/or the illumination device 44 located at the distal end 40 of the endoscope shaft 20. In the embodiment shown in FIG. 2, the electronics control mechanism 54 includes a first, e.g., a white balance control, button 541. In this embodiment, the white balance control button 541 functions to selectively control a white balancing operation by sending a corresponding signal to an image or video control unit (not shown), as is shown and described in greater detail in Applicant's co-pending patent application having a client matter number "EVO 1009-US", filed on the same date as this present application, which is hereby incorporated by reference herein in its entirety.

In the embodiment shown in FIG. 2, the electronics control mechanism 54 also includes a second, e.g., an image capture control, button 542. In this embodiment, the image capture control button 542 functions to selectively control the capture of image or video signals sent by the image capture device 44, e.g., such as by providing a signal to an image or video display or control unit (not shown), as is shown and described in greater detail in Applicant's co-pending patent application having a client matter number "EVO 1009-US".

In the embodiment shown in FIG. 2, the control region 502 also has the shaft steering mechanism 56. As set forth above, the shaft steering mechanism 56 includes various features, e.g., knobs, rollers, etc., that allow a user to control or steer the lateral displacement at the distal end 40 of the endoscope shaft 20. In the embodiment shown in FIG. 2, the shaft steering mechanism 56 includes a first knob 561 for controlling a first movement of the distal end 40 of the endoscope shaft 20. FIG. 2 also illustrates the shaft steering mechanism 56 including opposing roller knobs 562a, 562b (knob 562b being hidden from view in FIG. 2, but being located on the opposite side of the handle 50) for controlling additional movements of the distal end 40 of the endoscope shaft 20. Additional features and functionality of the shaft steering mechanisms 56 are shown and described in greater detail in Applicant's co-pending patent application having a client matter number "EVO 1008-US", filed on the same date as this present application, which is hereby incorporated by reference herein in its entirety.

In addition, in the embodiment shown in FIG. 2, the handle 50 of the trans-nasal endoscope 10 includes a connection to the AWS tubing set 35. As set forth above, the AWS tubing set includes various flexible tubes that connect to the suction source 36, the water source 37 and the air source 38, as will be described in greater detail below in connection with FIG. 7. Still further, the handle 50 includes a connection to a video display output 57, e.g., for connecting to and outputting image data to a separate video display or control unit (not shown in FIG. 2). In the embodiment shown in FIG. 2, the video display output 57 is bundled together with the AWS tubing set 35, as will be described in greater detail below in connection with FIG. 7.

Figure 3:
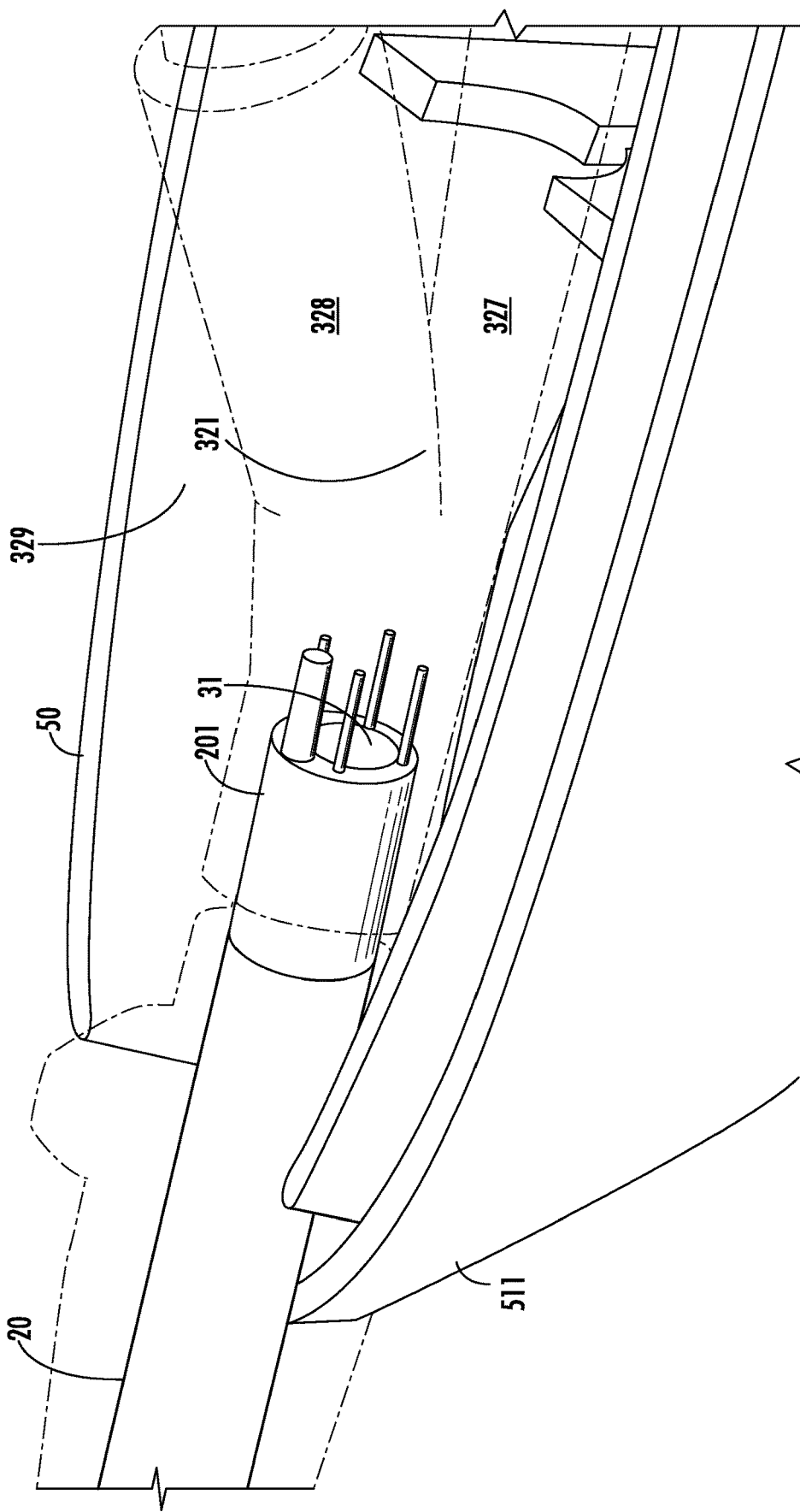
FIG. 3 is a perspective, cut-away view of the handle in the vicinity of a bifurcation region, with most of the features of the handle being hidden or shown in phantom so as not to obscure the features shown, in accordance with various embodiments.

FIG. 3 is a perspective, cut-away view of the handle 50 in the vicinity of the bifurcation region 32, with most of the features of the handle 50 being hidden or shown in phantom so as not to obscure the features shown. In the embodiment shown in FIG. 3, the proximal-most end 201 of the endoscope shaft 20 extends slightly proximal relative to the distal-most end 511 of the handle 50. The working channel 31 which extends longitudinally through the shaft 20 opens into a bifurcation fitting 329. The bifurcation fitting 329 is sealingly fitted onto the end 201 of the shaft 20. The bifurcation fitting 329 functions to split the working channel 31 into two channels within the handle 50.

The first channel 328 of the bifurcation fitting 329, in the embodiment shown, angles upwardly towards an instrument port, as will be shown and described in greater detail in connection with FIG. 4. The second channel 327 of the bifurcation fitting 329, in the embodiment shown, extends proximally from the working channel 31 towards the proximal end of the handle 50, where it communicates with a fluid control mechanism, as will be shown and described in greater detail in connection with FIGS. 5 and 6. Of course, it should be recognized that the bifurcation fitting 329 could connect to still other channels if desired, e.g., additional instrument ports or the like, or it could connect to the channels described hereinabove in various different orientations, depending on, e.g., the configuration of the handle 50 among other factors.

Figure 4:
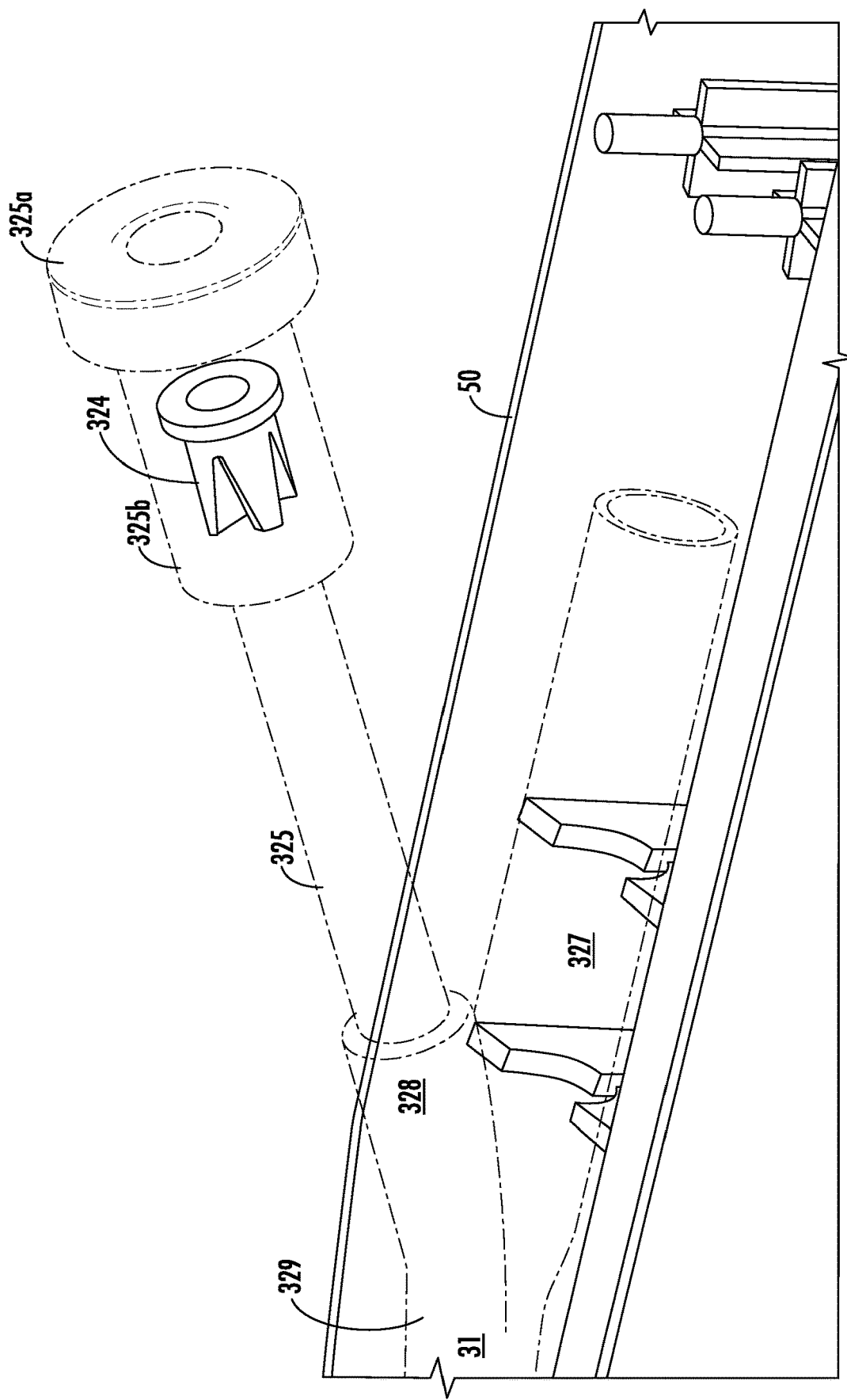
FIG. 4 is another perspective, cut-away view of the handle in the vicinity of the bifurcation region, but enlarged in comparison to FIG. 3 so as to show additional details of the various components of the handle, in accordance with various embodiments.

FIG. 4 is another perspective, cut-away view of the handle 50 in the vicinity of the bifurcation region 32, but enlarged in comparison to FIG. 3 so as to show additional details of the various components of the handle 50, but again with most of the features of the handle 50 being hidden or shown in phantom so as not to obscure the features shown. Specifically, it can be seen in FIG. 4 that the first channel 328 of the bifurcation fitting 329 connects to an instrument port 325. The instrument port 325 extends from the bifurcation fitting 329 within the handle 50 through an opening in the handle so as to provide a proximal end region 325a that is outside of the handle 50. The proximal end region 325a of the instrument port 325 includes a valve housing 325b in which resides an instrument port valve 324.

The instrument port 325 allows a surgical instrument (not shown) to be introduced into the proximal end region 325a, through the second channel 328 and into and through the working channel 31. The surgical instrument that is introduced and inserted through the working channel 31 via the instrument port 325 may be any conceivable surgical instrument that is sized and shaped to fit therethrough. For example, the instrument port 325 may be configured to receive a biopsy forceps instrument therethrough and into the working channel so as to perform a biopsy procedure on the patient's tissue at or near the distal end 40 of the shaft 20.

In various embodiments, the instrument port valve 324 positioned in the valve housing 325a at the proximal end of the instrument port 325 is configured to prevent the ingress of any foreign matter into the working channel 31 prior to, or during, a surgical instrument being inserted therethrough. In addition, the instrument port valve 324 also functions to prevent the flow of any fluids, e.g., air, water or suction, that may be inside the working channel 31 from escaping through the first channel 328 and out the proximal end region 325a of the instrument port 325. Advantageously, the instrument port valve 324 may be configured to prevent the escape of any such fluids, e.g., air, water or suction, that may be inside the working channel 31 when a surgical instrument is present within the first channel 328. Still further, the instrument port valve 324 may be configured to prevent the escape of any such fluids, e.g., air, water or suction, that may be inside the working channel 31 when no surgical instrument is present within the first channel 328. In some embodiments, a combination of valves may be employed, e.g., an instrument seal for sealing in the presence of an instrument and/or a separate zero seal for sealing the opening when no instrument is present therewithin. In some embodiments, the instrument port valve 324 may be configured as, e.g., a quad-port valve or "double-duckbill" valve, so as to provide a single valve that performs the functions of both an instrument seal, e.g., for sealing in the presence of an instrument, and a zero seal, e.g., for sealing the opening when no instrument is present therewithin.

As set forth above, in various embodiments, the handle 50 includes a bifurcation fitting 329 also having a second channel 327 configured to selectively convey at least one of air, suction or water into the working channel 31. As mentioned in connection with FIG. 2, the control region 502 of the handle 50 has an AWS control mechanism 52 that includes various features, e.g., buttons, valves, etc., that allow such selective connection of the air, water and suction supply sources 36, 37, 38 to the working channel 31 via the second channel 327 of the bifurcation fitting 329.

Figure 5:
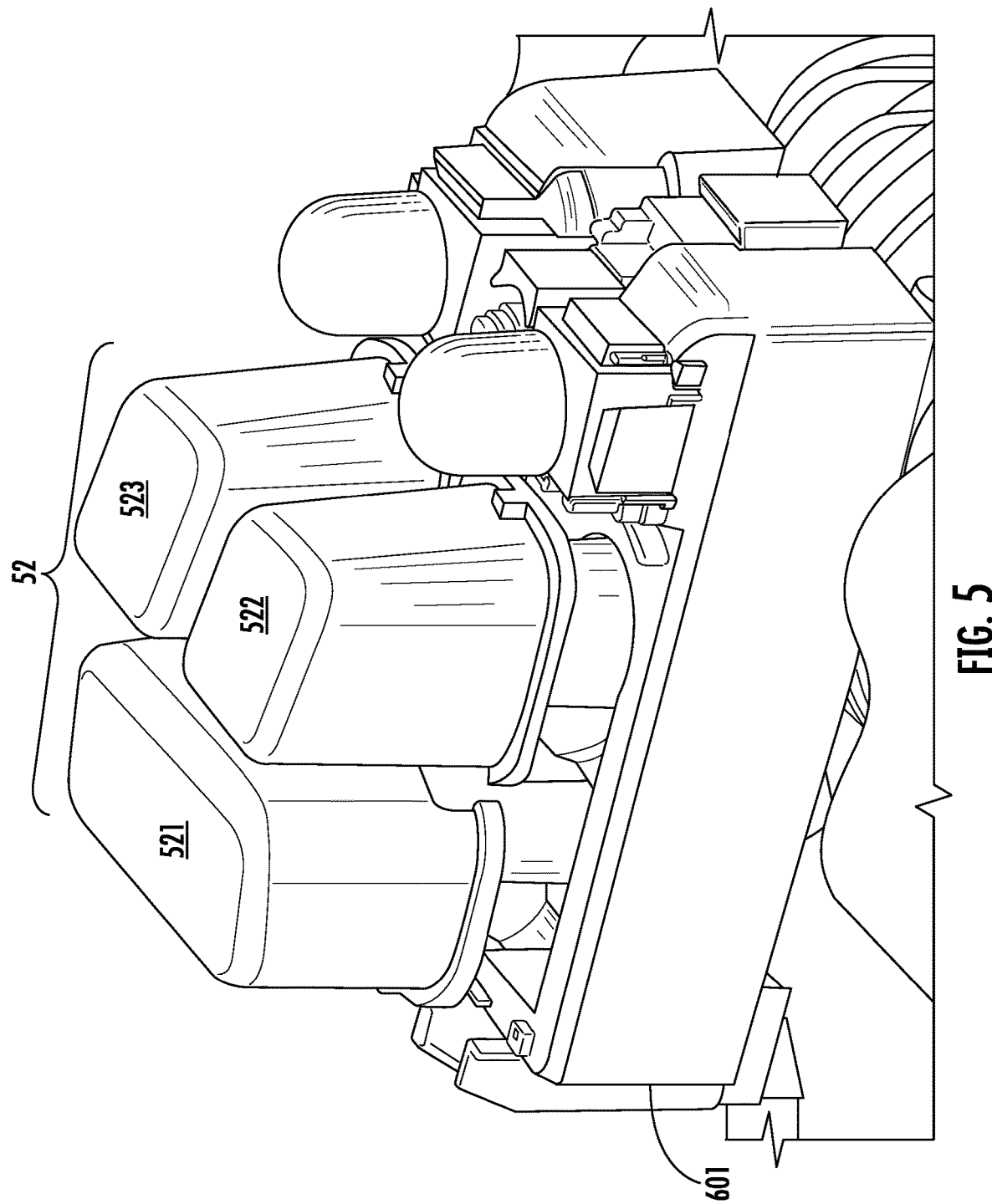
FIG. 5 is a perspective view of some components of an AWS control mechanism, in accordance with various embodiments.

FIG. 5 is a perspective view (with various components, such as the walls of the handle 50, being hidden so as not to obscure the features shown) of, among other components, an AWS control mechanism 52, according to an embodiment. FIG. 5 illustrates the AWS control mechanism 52 having a control manifold 601 on which are mounted various buttons that allow a user to selectively control the flow of air, suction and water into the working channel 31. In this embodiment, the AWS control mechanism 52 includes an air supply control button 521 that functions to selectively connect an air source, e.g., the air source 38 shown in FIG. 2, to the working channel 31. The AWS control mechanism 52 also includes a water supply control button 522 that functions to selectively connect a water source, e.g., the water source 37 shown in FIG. 2, to the working channel 31. Still further, the AWS control mechanism 52 may also include a suction supply control button 523 that functions to selectively connect a suction source, e.g., the suction source 36 shown in FIG. 2, to the working channel 31.

Figure 6:
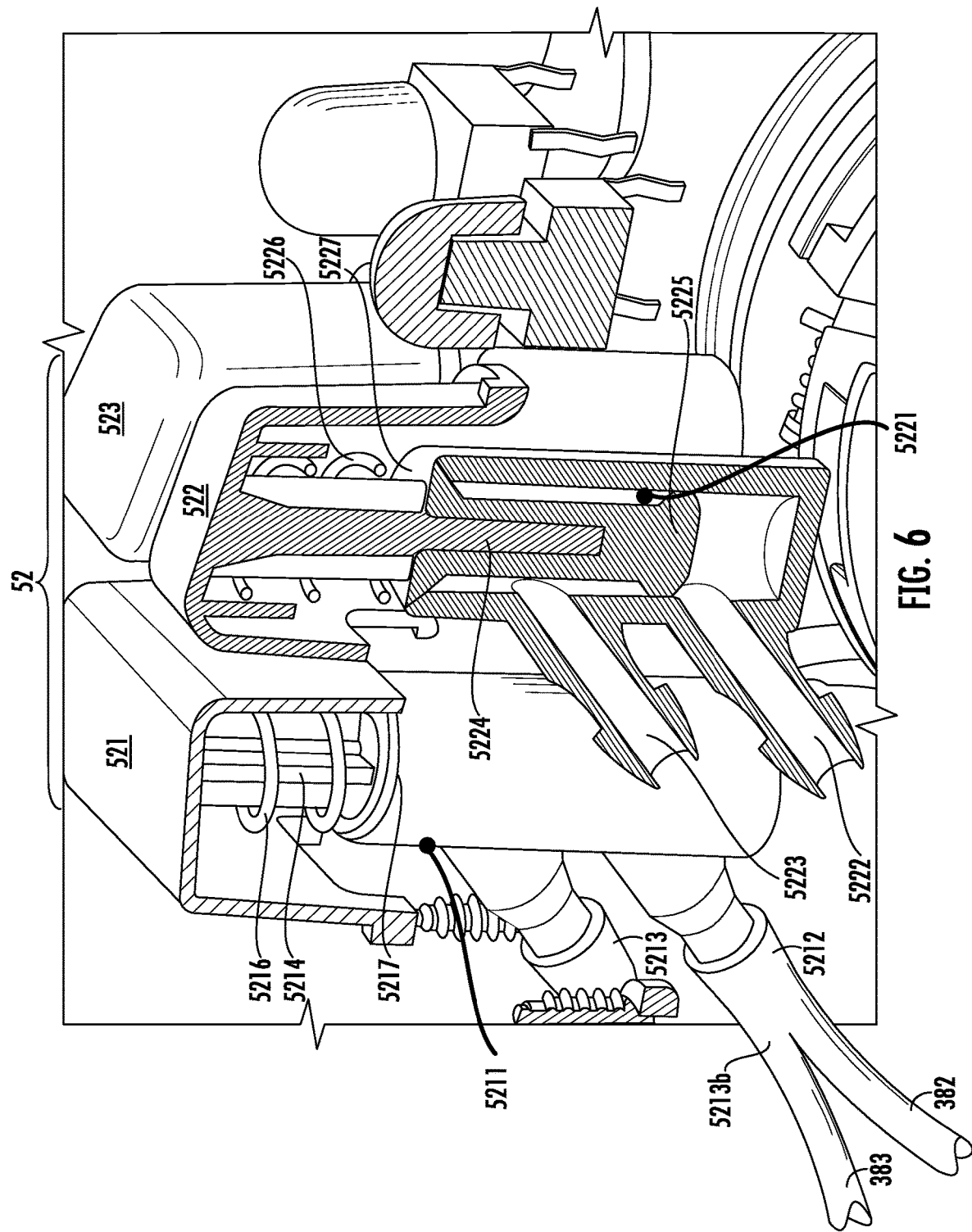
FIG. 6 is a perspective view similar to FIG. 5 but having certain features of the AWS control mechanism cut-away so as to show additional details thereof, in accordance with various embodiments.

FIG. 6 is a perspective view similar to FIG. 5 but having certain features cut-away so as to show additional details thereof (like FIG. 5, FIG. 6 also has certain features, such as the walls of the handle 50, being hidden so as not to obscure the features shown). Specifically, FIG. 6 illustrates the internal components of an AWS control mechanism 52, according to various embodiments.

For example, FIG. 6 illustrates the internal components of the water supply control button 522 that functions to selectively connect a water source, e.g., the water source 37 shown in FIG. 2, to the working channel 31. As shown, the water supply control button 522 is part of a water supply control valve 5221. The water supply control valve 5221 includes a water inlet 5222 that is connected to a source of water (not shown here) such as the water supply source 37 shown in FIG. 2. In addition, the water supply control valve 5221 may include a water outlet 5223 connected to the working channel 31 (not shown here). Still further, the water supply control valve 5221 may include a water valve sealing element 5224 that moves between closed and open positions.

FIG. 6 illustrates the water supply control valve 5221 in the closed position. In this closed position, a bottom sealing ridge 5225 of the water valve sealing element 5224 is positioned above the water inlet 5222, such that it seals against the inner walls of the water supply control valve 5221 in between the water inlet 5222 and the water outlet 5223. As such, the bottom sealing ridge 5225 of the water valve sealing element 5224 prevents water that is entering the water supply control valve 5221 via the water inlet 5222 from exiting the water supply control valve 5221 via the water outlet 5223.

As further shown in FIG. 6, the water supply control button 522 is attached to the water valve sealing element 5224. In addition, the water supply control valve 5221 includes a water valve spring 5226 that is interposed between the water supply control button 522 and a ridge 5227 on the body of the water supply control valve 5221. In this configuration, the water valve spring 5226 biases the water supply control button 522 upwardly, which, because of its attachment to the water valve sealing element 5224, also biases the water valve sealing element 5224 upwardly. In the absence of any force applied to the water valve spring 5226, the water supply control valve 5221 remains in this resting position, in which the water valve sealing element 5224 keeps the water supply control valve 5221 closed. By the water valve sealing element 5224 keeping the water supply control valve 5221 closed in this resting position, water is prevented from flowing from the water source through the water supply control valve 5221 and into the working channel 31 of the shaft 20.

FIG. 6 also illustrates the internal components of the air supply control button 521 that functions to selectively connect an air source, e.g., the air source 38 shown in FIG. 2, to the working channel 31. As shown, the air supply control button 521 is part of an air supply control valve 5211. The air supply control valve 5211 includes an air inlet 5212 that is connected to a source of air (not shown here) such as the air supply source 38 shown in FIG. 2. In addition, the air supply control valve 5211 may include an air outlet 5213 connected to the working channel 31 (not shown here). Still further, the air supply control valve 5211 may include an air valve sealing element 5214 (partially hidden in this view) that moves between closed and open positions.

FIG. 6 illustrates the air supply control valve 5211 in the closed position. In this closed position, a bottom sealing ridge (hidden in this view) of the air valve sealing element 5214 is positioned above the air inlet 5212, such that it seals against the inner walls of the air supply control valve 5211 in between the air inlet 5212 and the air outlet 5213. As such, the bottom sealing ridge of the air valve sealing element 5214 prevents air that is entering the air supply control valve 5211 via the air inlet 5212 from exiting the air supply control valve 5211 via the air outlet 5213.

As further shown in FIG. 6, the air supply control button 521 is attached to the air valve sealing element 5214. In addition, the air supply control valve 5211 includes an air valve spring 5216 that is interposed between the air supply control button 521 and a ridge 5217 on the body of the air supply control valve 5211. In this configuration, the air valve spring 5216 biases the air supply control button 521 upwardly, which, because of its attachment to the air valve sealing element 5214, also biases the air valve sealing element 5214 upwardly. In the absence of any force applied to the air valve spring 5216, the air supply control valve 5211 remains in this resting position, in which the air valve sealing element 5214 keeps the air supply control valve 5211 closed. By the air valve sealing element 5214 keeping the air supply control valve 5211 closed in this resting position, air is prevented from flowing from the air source through the air supply control valve 5211 and into the working channel 31 of the shaft 20.

Although hidden from view in FIG. 6, the suction supply button 523 of the AWS control mechanism 52 may have internal components similar to those described hereinabove for the water supply button 522 and the air supply button 521, and may thus function to selectively connect a suction source, e.g., the suction source 36 shown in FIG. 2, to the working channel 31 in the same way as described above for the water supply button 522 and the air supply button 521.

In order to operate the AWS control mechanism and thereby permit flow from the respective source of air, suction or water into and through the working channel 31, a user may press the buttons so as to open the valves. For example, in the embodiment shown in FIG. 6, in order to permit flow from the water source into and through the working channel 31, a user may press the water supply control button 522 downwardly with enough force to overcome the biasing force provided by the water valve spring 5226. Once the biasing force of the water valve spring 5226 is overcome, the water valve sealing element 5224 is moved downwardly until the bottom sealing ridge 5225 of the water valve sealing element 5224 is moved below the water valve inlet 5222. Once the bottom sealing ridge 5225 of the water valve sealing element 5224 is moved below the water valve inlet 5222, water entering the water valve inlet 5222 is now free to flow out of the water valve outlet 5223 by passing between the inner wall of the water supply control valve 5221 and the outer walls of the water valve sealing element 5224.

Likewise, in the embodiment shown in FIG. 6, in order to permit flow from the air source into and through the working channel 31, a user may press the air supply control button 521 downwardly with enough force to overcome the biasing force provided by the air valve spring 5216. Once the biasing force of the air valve spring 5216 is overcome, the air valve sealing element 5214 is moved downwardly until the bottom sealing ridge (not shown) of the air valve sealing element 5214 is moved below the air valve inlet 5212. Once the bottom sealing ridge of the air valve sealing element 5214 is moved below the air valve inlet 5212, air entering the air valve inlet 5212 is now free to flow out of the air valve outlet 5213 by passing between the inner wall of the air supply control valve 5211 and the outer walls of the air valve sealing element 5214. Still further, and although hidden from view in FIG. 6, in embodiments in which the suction supply button 523 of the AWS control mechanism 52 has internal components similar to those described hereinabove for the water supply button 522 and the air supply button 521, the suction supply button 523 may thus function to selectively open the suction supply control valve in the same way as described above for the water supply button 522 and the air supply button 521.

As set forth above, in embodiments, the various valves, e.g., the air supply control valve 521, the water supply control valve 522 and the suction supply control valve 523 of the AWS control mechanism 52, each have inlet openings that are connected to respective external air, water and suction supply sources 37, 38, 39. These respective inlet openings are connected to respective flexible tubes, which, as shown in FIG. 2, may collectively form an AWS tubing set 35 that connect to the handle 50 at a common opening in the handle 50. Of course, it should be recognized that, according to still other embodiments, the various tubes that connect the air, water and suction sources to their respective air, water and suction inlet openings need not connect to the handle 50 at a common opening, but may instead connect to the handle 50 at different locations.

Figure 7:
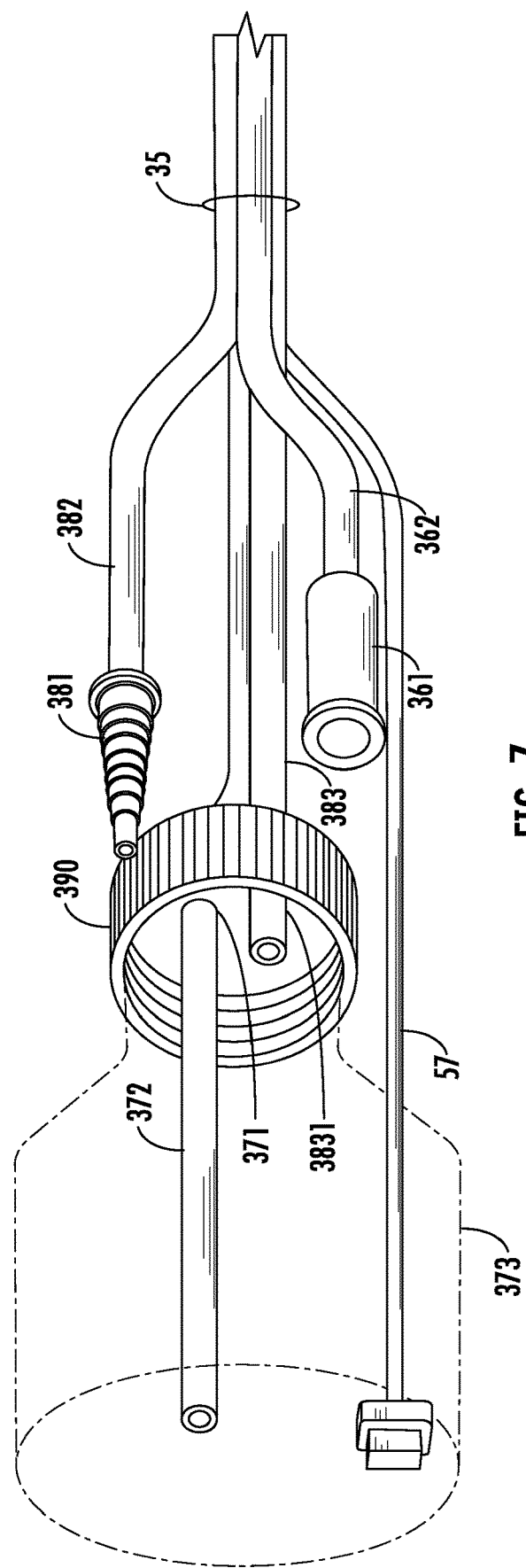
FIG. 7 is a perspective view of one end of an AWS tubing set, in accordance with various embodiments.

FIG. 7 is a perspective view of one end of an AWS tubing set 35, according to an embodiment thereof. In this embodiment, the AWS tubing set 35 includes a suction tube 362. One end of the suction tube 362 includes a connection fitting, e.g., suction tube connection fitting 361, that is configured to mate with a corresponding connection fitting on a suction source, e.g., suction source 36 shown in FIG. 2, which may be any conceivable suction supply such as a standard hospital suction connection, a suction tank or the like. The other end of the suction tube 362 is configured to be connected to the inlet opening of the suction supply control mechanism associated with the suction control button 523, as mentioned above.

Likewise, FIG. 7 illustrates a water tube 372. One end of the water tube 372 includes a connection fitting, e.g., water tube connection fitting 371, that is configured to mate with a corresponding connection fitting on a water source, e.g., water source 37 shown in FIG. 2. Water source 37 may be any conceivable water supply such as a standard hospital water connection, a water tank or the like. In an embodiment, the water source 37 may be a water bottle 373, which is shown in phantom in FIG. 7. The water bottle 373 may have a water bottle cap 390 configured to be selectively sealed onto the water bottle 373. The water bottle cap 390 may have the water tube connection fitting 371 thereon such that the water tube 372 may be selectively connected thereto. In the embodiment shown, the water tube 372 extends through the water tube connection fitting 371 such that the end of the water tube 372 is positioned close to the bottom of the water bottle 373, thereby enabling the water tube 372 to obtain water from the water bottle 373 regardless of how full the water bottle 372 is with water. The other end of the water tube 372 is configured to be connected to the water inlet 5222 of the water supply control valve 5221, as shown and described hereinabove in connection with FIG. 6.

Furthermore, FIG. 7 illustrates a first air tube 382. One end of the first air tube 382 includes a connection fitting, e.g., first air connection fitting 381, that is configured to mate with a corresponding connection fitting on an air source, e.g., air source 38 shown in FIG. 2. The air source 38 may be any conceivable air supply such as a standard hospital air connection, an air tank or the like. The other end of the first air tube 382 is configured to be connected to the air inlet 5212 of the air supply control valve 5211, as shown and described hereinabove in connection with FIG. 6.

Still further, FIG. 7 illustrates a second air tube 383. One end of the second air tube 383 includes a connection fitting, e.g., second air connection fitting 3831, that may be disposed on the bottle cap 390. In the embodiment shown, the second air tube 383 extends through the second air connection fitting 3831 such that the end of the second air tube 383 is positioned within the water bottle 373, thereby pressurizing the interior of the water bottle 373. By pressuring the interior of the water bottle 373, water is more forcefully and predictably pushed out of the water bottle 373 and into and through the water tube 372 to the water inlet 5222 of the water supply control valve 5221, thereby ensuring that water is available in the water supply control valve 5221 when a user presses the water supply control button 522, as shown and described hereinabove in connection with FIG. 6.

A second end of the second air tube 383 may also extend into the handle 50. In an embodiment, the second end of the second air tube 383 is connected to a second air outlet 5213b of the air supply control valve 5211. In such an embodiment, the second air outlet 5213b may be located below the bottom sealing ridge of the air valve sealing element 5214 when the air supply control valve 5211 is in the resting position, e.g., when a user has not applied to the air supply button 521 a force sufficient to overcome the air valve spring 5216. In this way, regardless of the position of the air valve sealing element (e.g., regardless of whether the user has pushed the air supply button 521), air is free to flow from the air supply source 38, through the first air supply tube 382, through the air inlet 5212 of the air supply control valve 5211, through the second air outlet 5213b of the air supply control valve 5211, through the second air tube 383, through the second air connection fitting 3831 and into the water bottle 373. In this manner, the interior of the water bottle 373 is continuously pressurized.

In still another embodiment, a configuration may be employed by which the user may selectively pressurize the interior of the water bottle 373. In such an embodiment, the second end of the second air tube 383 may be connected to a second air outlet (not shown) that is located above the bottom sealing ridge of the air valve sealing element 5214 when the air supply control valve 5211 is in the resting position, e.g., when a user has not applied to the air supply button 521 a force sufficient to overcome the air valve spring 5216. In this way, only after a user has applied sufficient pressure on the air supply valve 522 to overcome the biasing force of the air valve spring 5216, and thereby move the bottom sealing ridge of the air valve sealing element 5214 to a position that is below the first air inlet 5212, is air is free to flow from the air supply source 38, through the first air supply tube 382, through the first air inlet 5212 of the air supply control valve 5211, through the second air outlet of the air supply control valve 5211, through the second air tube 383, through the second air connection fitting 3831 and into the water bottle 373. In this manner, the interior of the water bottle 373 may be selectively pressurized by the user. Such selective pressurization of the water bottle 373 may be needed or desired when the level of water in the water bottle 373 is relatively low and the pressure in the water bottle 373 has decreased. Additional or alternatively, such selective pressurization of the water bottle 373 may be desirable so as to keep the pressure in the water bottle 373 low except immediately before a user desires to introduce water into the working channel 31.

FIG. 7 also illustrates that, in embodiments, the tube set 35 may also include a video display output cable 57. The video display output cable 57 may be configured to convey image data from the image capture device 44 at the distal end 40 of the endoscope shaft 20 to, e.g., a separate video display (not shown) in response to signals generated by a user activating the buttons on the electronics control module 54. In the embodiment shown in FIG. 7, the video display output 57 is bundled into the AWS tubing set 35 along with the suction tube 362, the water tube 372, the first air tube 382 and the second air tube 383. In addition, the video display output cable 57 may also exit the handle 50 at a common location as the suction tube 362, the water tube 372, the first air tube 382 and the second air tube 383, as shown in FIG. 2. However, it should be recognized that the video display output cable 57 may exit the handle 50 at a different location from, and may be separately disposed relative to the AWS tubing set 35, as the suction tube 362, the water tube 372, the first air tube 382 and the second air tube 383, depending on, e.g., the configuration of the handle 50, the location of the various external devices (e.g., the air, suction and water sources and/or the external video display device, etc.), among other factors.

Of course, it should also be recognized that, in alternative embodiments, the AWS tubing set 35 may have fewer flexible tubes than those described hereinabove, e.g., the tubing set may include only one or more of air, suction and/or water, but not all three. Still further, in still other embodiments, the AWS tubing set 35 may have other flexible tubes, in addition to those flexible tubes described hereinabove, e.g., the tubing set may have additional air tubes, additional water tubes, additional suction tubes, tubes for conveying other types of fluids such as carbon dioxide or gas or liquid therapeutics, etc.

There are no limitations in terms of the particular embodiments described in this application, which are intended as illustrations of various aspects only. Many modifications and variations can be made without departing from its spirit and scope, as will be apparent to those skilled in the art. Functionally equivalent methods and apparatuses, in addition to those enumerated herein, will be apparent to those skilled in the art from the foregoing descriptions. Such modifications and variations are intended to fall within the scope of the appended claims. Only the terms of the appended claims are intended to be limiting, along with the full scope of equivalents to which such claims are entitled. It is also to be understood that the terminology used herein, e.g., "and", "or", "including", "at least" as well as the use of plural or singular forms, etc., is for the purpose of describing examples of embodiments and is not intended to be limiting.

What is claimed is:

1. An endoscope for use in a surgical procedure, comprising:
   a handle for gripping by a user;
   a shaft extending from the handle, the shaft defining an inner wall that forms a common working channel extending longitudinally therethrough, the common working channel configured to directly receive an instrument therethrough, the shaft having a distal region configured to be inserted into a patient; and
   a fluid control valve arrangement on the handle, the fluid control valve arrangement including first, second and third valves each of which includes a spring that biases the valves toward their respective resting positions, each spring having a button mounted thereto that, upon being pressed by the user, overcomes the bias of the spring to move the valve from a closed position to an open position at which an inlet opening is connected to an outlet opening to thereby permit flow from respective sources of air, suction and water into and through the common working channel, wherein the first valve is an air valve;

an air valve inlet;

a first air tube connected to the air valve inlet for conveying air into the common working channel;

a second air tube having an outlet connected to the air valve inlet of the first valve for conveying air to a water source for pressurizing the water source.

2. The endoscope of claim 1, wherein the fluid control valve arrangement is actuatable by the user to selectively control the flow of air, suction and water through the working channel.

3. The endoscope of claim 2, wherein the second valve is actuatable by the user to selectively control the flow of suction through the working channel, and the third valve is actuatable by the user to selectively control the flow of water through the working channel.

4. The endoscope of claim 3, wherein each of the first, second and third valves includes an inlet connected to the respective source of air, suction and water, and an outlet connected to the working channel.

5. The endoscope of claim 4, each of the first, second and third valves also including a sealing element that, when the valve is in a rest position, is in a closed position at which the inlet opening is not connected to the outlet opening.

6. The endoscope of claim 1, wherein the working channel includes an instrument port through which a surgical instrument can be introduced into and through the working channel.

7. The endoscope of claim 1, wherein the working channel includes a bifurcation region that splits the working channel into a first channel and a second channel, the first channel having an instrument port through which a surgical instrument can be introduced into the working channel, and the second channel connected to the fluid control valve arrangement on the handle for selectively controlling the flow of the at least one of air, suction or water into the working channel.

8. The endoscope of claim 7, wherein the instrument port includes a valve through which the surgical instrument can be introduced, the instrument port valve being configured to prevent flow of air, water or suction through the first channel when the surgical instrument is present within the first channel and when the instrument is not present in the first channel.

9. The endoscope of claim 1, wherein the shaft is configured for use in pediatric trans-nasal endoscopy procedures.

10. An endoscope for use in a surgical procedure, comprising:

a handle for gripping by a user, the handle including:
 an air valve;
 an air valve inlet;
a shaft extending from the handle, the shaft having a working channel extending longitudinally therethrough, the shaft having a distal region configured to be inserted into a patient; and
a tubing set connected to the handle, the tubing set including:
 a suction tube configured to generate suction in the working channel;
 a water tube configured to convey water from a water source towards the working channel;
 a first air tube connected to the air valve inlet to convey air from an air source to the working channel; and
 a second air tube connected via its outlet to the air valve inlet to convey air from the air source to the water source so as to pressurize the water source and thereby push water from the water source towards the working channel.

11. The endoscope of claim 10, wherein the water source is a water bottle.

12. The endoscope of claim 11, wherein the water bottle has a cap that defines a first connection to the water tube and a second connection to the second air tube.

13. The endoscope of claim 10, further comprising:
a fluid control valve arrangement on the handle actuatable by the user to selectively control the flow of the air from the air source to the working channel, the flow of suction from the working channel to a suction source, and the flow of water from the water source to the working channel.

14. The endoscope of claim 13, wherein the fluid control valve arrangement includes the air valve actuatable by the user to selectively control the flow of air through the working channel, a second valve actuatable by the user to selectively control the flow of suction through the working channel, and a third valve actuatable by the user to selectively control the flow of water through the working channel.

15. The endoscope of claim 10, wherein the tubing set further comprises a video connector cable.

16. The endoscope of claim 15, further comprising:
an illumination source and an imaging device located at the distal end of the shaft, the illumination source and the imaging device being connected to, and at least partially controlled by an electronic control button arrangement on the handle,
wherein the video connector cable conveys signals from the electronic control button arrangement on the handle to an external video display device.

17. The endoscope of claim 10, wherein the shaft is configured for use in pediatric trans-nasal endoscopy procedures.

\* \* \* \* \*